United States Patent [19]

Lee

[11] Patent Number: 5,470,568
[45] Date of Patent: Nov. 28, 1995

[54] METHODS AND COMPOSITIONS OF A POLYMER (POLOXAMER) FOR CELL REPAIR

[75] Inventor: Raphael C. Lee, Chicago, Ill.

[73] Assignee: Arch Development Corporation, Chicago, Ill.

[21] Appl. No.: 835,271

[22] Filed: Feb. 13, 1992

[51] Int. Cl.$^6$ ............... A61K 9/06; A61K 9/12; A61K 31/77
[52] U.S. Cl. ............ 424/78.02; 424/78.17; 424/45; 424/78.06; 424/422; 424/DIG. 13; 514/917; 514/975; 935/52; 935/93; 935/95; 604/20; 252/70; 106/13
[58] Field of Search ............ 424/78.02, 78.06, 424/78.08, 78.17, 78.37, 78.06, 43, 45, 422; D16/13; 514/917, 975; 935/52, 53, 55, 93, 95, 96; 604/20; 252/70; 106/13

[56] References Cited

U.S. PATENT DOCUMENTS

| | | | |
|---|---|---|---|
| 29,909 | 2/1879 | Kartz | 252/89 |
| 2,674,619 | 4/1954 | Lundsted | 260/485 |
| 2,854,378 | 11/1958 | Buckwalter | 167/64 |
| 3,089,818 | 5/1963 | Stone | 167/65 |
| 3,140,232 | 7/1964 | Noseworthy | 167/65 |
| 3,577,522 | 5/1971 | Hymes | 436/78 |
| 3,590,125 | 6/1971 | Hymes | 424/78 |
| 3,641,240 | 2/1972 | Hymes | 434/78 |
| 3,740,421 | 11/1966 | Schmolka | 424/65 |
| 3,867,521 | 6/1973 | Miskel et al. | 424/37 |
| 3,956,259 | 5/1976 | Garcia et al. | 260/112 |
| 3,980,772 | 11/1976 | Ginger et al. | 424/94 |
| 4,073,886 | 2/1978 | Kehm | 260/112 |
| 4,100,271 | 7/1978 | Krezanoski | 424/78 |
| 4,105,650 | 8/1978 | Shanbrom et al. | 260/112 |
| 4,179,337 | 12/1979 | Davis et al. | 435/181 |
| 4,186,253 | 1/1980 | Yokoyama et al. | 436/240 |
| 4,305,922 | 12/1981 | Rhodes | 424/1 |
| 4,395,393 | 7/1983 | Schmolka | 424/78 |
| 4,407,790 | 10/1983 | Oakes et al. | 424/78 |
| 4,600,652 | 7/1986 | Solomon et al. | 428/423 |
| 4,801,452 | 1/1989 | Hunter et al. | 424/94.63 |
| 4,837,014 | 6/1989 | Hunter et al. | 424/78 |
| 4,873,083 | 10/1989 | Hunter et al. | 424/83 |
| 4,879,109 | 11/1989 | Hunter | 424/83 |
| 4,897,263 | 1/1990 | Hunter | 424/83 |
| 4,937,070 | 6/1990 | Hunter | 424/83 |
| 4,997,664 | 3/1991 | Hunter | 424/83 |
| 5,002,965 | 3/1991 | Ramwell et al. | 514/468 |
| 5,017,370 | 5/1991 | Hunter | 424/83 |
| 5,028,599 | 7/1991 | Hunter | 514/821 |
| 5,030,448 | 7/1991 | Hunter | 424/83 |
| 5,032,394 | 7/1991 | Hunter | 424/83 |
| 5,039,520 | 8/1991 | Hunter | 424/83 |
| 5,041,288 | 8/1991 | Hunter | 424/83 |
| 5,045,468 | 9/1991 | Darfler | 435/240.27 |
| 5,047,236 | 9/1991 | Hunter et al. | 424/83 |
| 5,064,643 | 11/1991 | Hunter et al. | 424/83 |
| 5,071,649 | 12/1991 | Hunter | 424/78.38 |
| 5,075,333 | 12/1991 | Bryce et al. | 514/706 |
| 5,078,995 | 1/1992 | Hunter et al. | 424/78.38 |
| 5,080,894 | 1/1992 | Hunter et al. | 424/78.38 |
| 5,089,260 | 2/1992 | Hunter et al. | 424/78.38 |
| 5,152,979 | 10/1992 | Hunter | 424/78.38 |

FOREIGN PATENT DOCUMENTS

| | | |
|---|---|---|
| 43628/68 | 11/1968 | Australia . |
| 0200467A3 | 4/1986 | European Pat. Off. . |
| 2267112 | 4/1975 | France . |
| 1930957 | 6/1969 | Germany . |
| WO8502116 | 5/1985 | WIPO . |
| WO87/06836 | 11/1987 | WIPO . |
| WO87/06831 | 11/1987 | WIPO . |

OTHER PUBLICATIONS

Benner et al., "Uber die Wirkung von Pluronic F68, einem Polyoxypropylen–Polyoxyathylen–Kondensat, auf die ADP–induzierte Thrombocytenaggregation in vitro," *Pfungers Arch.*, 315:45–52, 1970.

Block et al., "Acutely Traumatized Canine Ureter," *Urology*, III(2):190–194, 1974.

Sugi et al., "The Use of Fluosol (TM)–DA 20% (FDA) in Emergency Situations: A Report of 67 Clinical Cases," (Abstract), International Symposium on Advances in Blood Substitute Research, San Francisco, California, Sep. 29–Oct. 1, 1982, Alan R. Liss, Inc., New York.

Ceresa, "The Application of Block Copolymer Polyol Surfactants," *Block and Graft Copolymerization*, 2:174–272, 1976.

Kanter et al., "Superiority of Perfluorocarbon Cardioplegia Over Blood or Crystalloid Cardioplegia," *Circulation*, 64 (II):76–80, 1987.

Reindorf et al., "Perfluorocarbon Compounds: Effects on the Rheological Properties of Sickle Erythrocytes In Vitro," *American Journal of Hematology*, 19:229–236, 1985.

Spiess et al., "Protection from with Perfluorocarbons in Rabbits," *Stroke*, 17(6):1146–1149, 1986.

(List continued on next page.)

*Primary Examiner*—Edward Webman
*Attorney, Agent, or Firm*—Arnold, White & Durkee

[57] ABSTRACT

Novel methods for prophylaxis and treatment of tissue damage resulting from cell membrane permeabilization are disclosed. Compositions comprising a surface active copolymer are employed to prevent permeabilization or to promote membrane repair. Methods for enhancement of cell survival following membrane permeabilization in vitro are also disclosed, along with methods for increasing the efficacy of transfection of cells with foreign exogenous macromolecules, in particular DNA, also involving treatment of permeabilized cells with a surface active copolymer. Also disclosed are novel methods for prophylaxis and treatment of tissue damage, and for enhancement of cell survival and transfection efficacy, using a surface active copolymer in combination with high energy phosphate compounds which are capable of recharging cellular energy stores and thereby potentiating cell repair and survival. Compositions comprising surface active copolymers for intravenous, intramuscular, and topical use are also disclosed, along with novel compositions comprising a combination of a surface active copolymer and a high energy phosphate compound.

40 Claims, No Drawings

OTHER PUBLICATIONS

Thomas and Lamkin, "Paralysis of Phagocyte Migration Due to an Artificial Blood Substitute," *Bood,* 64(2):400–405, 1984.

Tokioka et al., "Effects of intracoronary infusion of arterial blood or Fluosol–DA 20% on regional myocardial metabolism and function during brief coronary artery occlusions," *Circulation,* 75(2):473–481, 1987.

Vercellott et al., "Activation of Plasma Complement by Perfluorocarbon Artificial Blood: Probable Mechanism of Adverse Pulmonary Reactions in Treated Patients and Rationale for Corticosteroid Prophylaxis," *Blood,* 59(6):1299–1304, 1982.

Tabuchi et al., "Use of Fluosol (TM)–DA 20% (FDA) as a Perfusate to Prevent Ischemic GI Damage," (Abstract), International Symposium on Advances in Blood Substitute Research, San Francisco, California, Sep. 29–Oct. 1, 1982, Alan R. Liss, Inc. New York.

Pluronic & Tetronic Block Copolymer Surfactants, BASF Technical Brochure, 1989.

Benner and Brunner, "Cold–Induced Platelet Aggregation In Vivo and its Inhibition by a Nonionic Surface Active Sustance," *Thrombosis Research,* 2:331–342, 1973.

Block et al., "Acutely Traumatized Canine Ureter," *Urology,* III(2):190–194, 1974.

Chesebro et al., "Restenosis After Arterial Angioplasty: A Hemorheologic Response to Injury," *Am. J. Cardiol.,* 60:10B–16B, 1987.

Danielson et al., "Use of Pluronic F–68 to Diminish Fat Emboli and Hemolysis During Cardiopulmonary Bypass," *The Journal of Thoracic and Cardiovascular Surgery,* 59(2):178–184, 1970.

Divertie and Petty, "Adult Respiratory Distress Syndrome," *Current Concepts.*

Forman et al., "Beneficial Long–Term Effect of Intracoronary Perfluorochemical on Infarct Size and Ventricular Function in a Canine Reperfusion Model," *JACC,* 9(5):1082–1090, 1987.

Forman et al., "Reduction of infarct size with intracoronary perfluorochemical in a canine preparation of reperfusion," *Circulation,* 71(5):1060–1068, 1985.

Geyer, "Potential uses of artificial blood substitutes," *Federation Proceedings,* 34(6):1525–1528, 1975.

Goodman et al., "Perfluorocarbon Emulsions in Cancer Therapy: Preliminary Observations on Presently Available Formulations," *Int. Biol. Phys.,* 10:1421–1424, 1984.

Grover et al., "The Effect6 of Pluronic F–68 on Circulatory Dynamics and Renal and Carotid Artery Flow During Hemorrhagic Shock," *Journal of Surgical Research,* 17:30–35, 1974.

Grover et al., "A Nonionic Surfactant and Blood Viscosity," *Arch. Surg.,* 106:307–310, 1973.

Grover et al., "Beneficial Effect of Pluronic F–68 on the Microcirculation in Experimental Hemorrhagic Shock," *Surgical Forum,* 30–32.

Harjula et al., "Perfluorocarbon Solution as a Myocardial Preservative," *Journal of Applied Cardiology,* 2(2):121–136, 1987.

Heron and Paton, "A Method for Measuring a Nonionic Surface–Active Agent (Pluronic F–68) in Biological Fluids," *Analytical Biochemistry,* 24:491–495, 1968.

Heinz et al., "Short– and Long–term Changes in Myocardial Perfusion After Percutaneous Transluminal Coronary Angioplasty Assessed by Thallium–201 Exercise Scintigraphy," *Ciculation,* 63(5):1001–1007, 1981.

Hoie and Schenk, "Effects of Pluronic F 68, Poloralkol, on Vascular Resistance In Vivo," *Journal of Surgical Research,* 11(10):515–517, 1971.

Hymes et al., "Influence of an industrial surfactant (pluronic F–68) on human amniotic fluid embolism," *Amer. J. Obstet. Gynec.,* 107(8):1217–1222, 1970.

Hymes et al., "The Influence of an Industrial Surfactant Pluronic F–68 in the Treatment of Hemorrhagic Shock," *Journal of Surgical Research,* 11(4):191–197, 1971.

Justice et al., "Prevention of Thrombosis with Agents Which Reduce Platelet Adhesiveness," *The American Surgeon,* 186–189, 1974.

Katzenstein et al., "Diffuse Alveolar Damage—The Role of Oxygen, Shock, and Related Factors," *American Journal of Pathology,* 85(1):210–224, 1976.

Ketchum et al., "Experimental Use of Pluronic F–68 in Microvascular Surgery," *Plastic & Reconstructive Surgery,* 53(3):288–292, 1974.

Ketchum, "Pharmacological alternations in the clotting mechanism: Use in microvascular surgery," *The Journal of Hand Surgery,* 3(5):407415, 1978.

Kunicki et al., "A Study of Variables Affecting the Quality of Platelets Stored at 'Romm Temperature'," *Transfusion,* 15(5):414–422, 1975.

Lane and Krukonis, "Reduction in the toxicity of a component of an artificial blood substitute by supercritical fluid fractionation," *Transfusion,* 28(4):375–378, 1988.

McBride et al., "Restenosis after Successful Coronary Angioplasty," *The New England Journal of Medicine,* 318(6):1734–1737, 1988.

Moore et al., "Reduction of Splenic Vascular Resistance During Perfusion by Pluronic F68," *Journal of Surgical Research,* 8(12):563–566, 1968.

Murray et al., "An Expanded Definition of the Adult Respiratory Distress Syndrome," *Am. Rev. Respir. Dis.,* 138:720–723, 1988.

Naito and Yokoyama, "Perfluorochemical Blood Substitutes FC–43 Emulsion Fluosol–DA, 20% and 35%," *Technical Information* 5:1–176, 1978.

Padilla et al., "Effect of fluorocarbon emulsions on the mechanical fragility of normal and sickle cells: in vitro studies," *Federation Proceedings,* 34(8):1510–1512, 1975.

Paton et al., "The Use of a Nonionic Detergent Added to Organ Perfusates," *Organ Perfusion and Preservation,* 105–120, Date?.

Prida et al., "Percutaneous Transluminal Coronary Angioplasty in Evolving Acute Myocardial Infarction," *The American Journal of Cardiology,* 57:1069–1074, 1986.

Repine et al., "Pulmonary Oxygen Toxicity and Ischemia–Reperfusion Injury," *Am. Rev. Respir. Dis.,* 136:483–485, 1987.

Richard and Sanders, "Effect of Lysine and Wetting Agents on Activated Plasminogen Solutions," *Canadian Journal of Biochemistry and Physiology,* 41:211–217, 1963.

Rodeheaver et al., "Pluronic F–68: A Promising New Skin Wound Cleanser," *Ann. Emerg. Med.,* 9(11):572–576, 1980.

Schmolka, "Artificial Skin I. Preparation and Properties of Pluonic F–127 Gels for Treatment of Burns," *J. Biomed. Mater. Res.,* 6:571–582, 1972.

Schwartz et al., "Aspirin and Dipyridamole in the Prevention of Restenosis after Percutaneous Transluminal Coronary Angioplasty," *The New England Journal of Medicine,* 318(26):1714–1719, 1988.

Smillie et al., "Cryopreservation of Human Platelet with

Polyvinylpyrrolidone," *Transfusion*, 21(5):552–556, 1981.

Smith et al., "Pluronic F–68, A non–ionic emulsifier, reduces the adhesivity of liganded sickle erythrocytes," *6th Int. Congress Biorheology Abstracts*, 23(3):238.

Thomas and Lamkin, "Paralysis of Phagocyte Migration Due to an Artificial Blood Substitute," *Bood*, 64(2):400–405, 1984.

Uno et al., "Determination of Surface–active Agents. Infrared Determination of the Proportion of Ethylene Oxide and Propylene Oxide in Pluronic," *Chem. Pharm. Bull.*, 15(1):77–82, 1987.

Vasko et al., "Poloxalkol Pluronic F–68: A Priming Solution for Cardiopulmonary Bypass."

Williams Jr. et al., "Modulation of Rat Granulocyte Traffic by a Surface Active Agent In Vitro and Bleomycin Injury," *Proceedings of the Society for Experimental Biology and Medicine*, 188:461–470, 1988.

Ohta, Hiromichi, et al., "The Long Term Effects of Percutaneous Transluminal Angioplasty for Treating Patients with Renovascular Hypertension: Case Studies," *The Journal of Vascular Diseases*, 535–542, 1986.

"Pilot studies on the safety of PFC Emulsion", 39–176, (author & journal unknown).

Aldwinckle et al., "Effects of Poly(Ethylene Glycol) on Liposomes and Erythrocytes: Permeability Changes and Membrane Fusion," *Biochimica et Biophysica Acta*, 689:548–560, 1982.

Arnold et al., "The Dielectric Properties of Aqueous Solutions of Poly(Ethylene Glycol) and Their Influence on Membrane Structure," *Biochimica et Biophysica Acta*, 815:515–518, 1985.

Arnold et al., "Effect of Poly(Ethylene Glycol) on Phospholipid Hydration and Polarity of the External Phase," *Biochimica et Biophysica Acta*, 728:121–128, 1983.

Bahnson & Boggs, "Addition of Serum to Electroporated Cells Enhances Survival and Transfection Efficiency," *Biochemical and Biophysical Research Communications*, 171(2):752–757, 1990.

Behr et al., "Efficient Gene Transfer Into Mammalian Primary Endocrine Cells with Lipopolyamine–Coated DNA," *Proceedings of the National Academy of Science USA*, 86:6982–6986, 1989.

Boni et al., "Lipid–Polyethylene Glycol Interactions: I. Induction of Fusion Between Liposmers," *Journal of Membrane Biology*, 62:65–70, 1981.

Boni et al., "Lipid–Polyethylene Glycol Interactions: II. Formation of Defects in Bilayers," *Journal of Membrane Biology*, 62:71–77, 1981.Chaudry et al., "ATP–MgCl$_2$ Infusion in Man: Increased Cardiace Output Without Adverse Systemic Hemodynamic Effects," *Surgical Forum*, 35:14–16, 1984.

Chaudry et al., "Effect of Adenosine Triphosphate–Magnesium Chloride Adminstration in Shock," *Surgery*, 75(2):220–227, 1974.

Gaehtgens & Benner, "Desaggregation of Human Red Blood Cells by Various Surface–Active Agents as Related to Changes of Cell Shape and Hemolysis," *Acta Haemat.*, 53:82–89, 1975.

Hirasawa et al., "Improved Survival and Reticuloendothelial Function with Intravenous ATP–MgCl$_2$ Following Hemorrhagic Shock," *Circulation Shock*, 11(2):141–148, 1983.

Janoff et al., "The Modification of Human Erythrocyte Membrane Structure by Membrane Stabilizers: An Electron Sprin Resonance Study," *American Journal of Hematology*, 10:171–179, 1981.

Knize et al., "Use of Antisludging Agents in Experiemental Cold Injuries," *Surgery, Gynecology & Obstetrics*, 129:1019–1026, 1969.

Loeffler et al., "Lipopolyamine–Mediated Transfection Allows Gene Expression Studies in Primary Neuronal Cells," *Journal of Neurochemistry*, 54(5):1812–1815, 1990.

McNeil, "Cell Wounding and Healing," *American Scientist*, 79:222–235, 1991.

Minetti et al., "Interaction of Neutral Polysaccharides with Phosphatidylcholine Multilamellar Liposomes. Phase Transitions Studied by the Binding of Fluorescein–Conjugated Dextrans," *Biochemistry*, 18(12):2541–2548, 1979.

Papahadjopoulos et al., "Molecular Mechanisms of Calcium–Induced Membrane Fusion," *Journal of Bioenergetics and Biomembranes*, 22(2):157–179, 1990.

Peters, "Biology of Radiation Therapy," *In Comprehensive Management of Head and Neck Tumors*, Eds., S. E. Thawley & W. R. Penje, W. B. Saunders Company, 1:132–152, 1987.

Rols & Teissié, "Electropermeabilization of Mammalian Cells: Quantitative Analysis of Phenomenon" *Biophysical Journal*, 58:1089– 1098, 1990.

Sáez et al., "Detergent–Like Properties of Polyethyleneglycols in Relation to Model Membranes," *FEBS Letters*, 137(2):323–326, 1982.

Schmolka, "A Review of Block Polymer Surfactants," *Journal of the American Oil Chemists' Society*, 54:110–116, 1977.

Sowers, "The Mechanism of Electroporation and Electrofusion in Erythrocyte Membranes," *In: Electroporation and Electrofusion in Cell Biology*, Neumann et al. eds., Plenum Publishing Corporation, pp. 229–256, 1989.

Tsong, "Electroporation of Cell Membranes," *Biophysical Journal*, 60:297–306, 1991.

Wang et al., "ATP–MgCl$_2$ Restores the Depressed Hepatocellular Function and Hepatic Blood Flow Following Hemorrhage and Resuscitation," *Journal of Surgical Research*, 50(4):368–374, 1991.

The Scientific Basis for the Biologic Activities of RheothRx™ Copolymer: A Rheologic, Antithrombotic and Cytoprotective Preparation, CytRx® Corporation.

METHODS AND COMPOSITIONS OF A POLYMER (POLOXAMER) FOR CELL REPAIR

BACKGROUND OF THE INVENTION

I. Field of the Invention

The present invention is directed to methods and compositions for prophylaxis and treatment of cell membrane damage, and resultant tissue injury, caused by external sources capable of disrupting cell membrane integrity. In particular embodiments, the present invention relates to methods of prophylaxis and/or treatment of tissue damage at the cell membrane level caused by radiation, freezing, or certain types of mechanical forces, and to the enhancement of cell survival and transfection efficacy, through the sealing of permeabilized cell membranes with an effective amount of a composition comprising a surface-active copolymer, preferably through pretreatment or concomitant treatment of injured tissue or permeabilized and transfected cells with high energy phosphate compounds.

II. Background of the Invention

The widespread clinical use of radiation therapy in the treatment of cancer, and the increasing interest in medicine and the biological sciences in methods involving the insertion of foreign molecules into living cells, have surprisingly led to a common problem which the present invention addresses. That problem involves damage to the membranes of cells in the nature of membrane permeabilization, or the production of discrete openings at numerous sites in the cells' membranes. The consequences of membrane permeabilization are numerous, and include loss of cytoplasm and some of the contents thereof, disruption of ionic concentration gradients, and depletion of intracellular energy stores.

In radiation therapy cells in normal tissue within the radiation field often suffer cell membrane permeabilization. The permeabilized cells may thereafter die and the tissue will subsequently undergo necrosis. In the laboratory, the methodologies typically used to insert foreign molecules into cells often involve the deliberate permeabilization of the cells' membranes, the openings serving as a site of ingress for the foreign molecules. As noted, however, one of the consequences of the permeabilization is concomitant egress of the contents of the cell, and without some means of potentiating the repair of the openings, cell survival rates can often be unacceptably low.

One of the more serious consequences of cell membrane permeabilization is the significant depletion of intracellular energy stores. Under normal circumstances, cells maintain a high level of ATP by using oxidizable substrates as sources of free energy. Following permeabilization, a great deal of energy would be expended in the cells' attempts to maintain intracellular ionic balances as ions move through openings in the cell membrane down their concentration gradients. As the intracellular ionic environment is disrupted, the normally occurring intracellular reactions which regenerate ATP stores will be inhibited, and as energy-dependent cellular processes continue, both to maintain cellular function and to attempt to repair the damage to the cell, the cells' ATP stores will be depleted further. This can result in the cells' inability to synthesize macromolecules necessary for continued cellular function, their inability to re-establish the proper ionic gradients across the membrane, and finally cell death.

A system in which such a depletion of ATP has been well demonstrated is in animals suffering hemorrhagic shock. It has been demonstrated that administration of ATP-$MgCl_2$ before, during, and even after a period of severe shock in rats had a beneficial effect on the animals' survival. The ATP was administered along with the $MgCl_2$ in order to prevent chelation of divalent cations from the vascular system by ATP administered alone. Furthermore, $MgCl_2$ inhibits the deamination and dephosphorylation of ATP. Thus, by administering equimolar amounts of ATP and $MgCl_2$, a higher concentration of ATP will be available to the tissues than if the ATP were administered alone. The results of this study suggested that the beneficial action of ATP-$MgCl_2$ may not have been through vasodilation alone, and it was postulated that the administered ATP could have a "priming effect" on the intracellular synthesis of ATP (1).

The actual method of cell membrane repair in vivo remains unknown, although researchers have made some inroads toward understanding the mechanisms involved. Calcium ions have been implicated, through both in vitro and in vivo studies, as having a critical role in membrane fusion and repair (2,3,4). Membrane and cytoskeletal proteins, including spectrin, dystrophin, and actin are probably also actively involved in the maintenance and repair of the cell membrane in vivo (4). Finally, it has also been suggested that chemical factors may play a signal-like role in wound healing at the cellular level (4). The present invention provides a method for minimizing radiation-induced damage via prophylaxis or via potentiation of cell membrane repair by post-exposure treatment with a surface active copolymer, as well as a method for potentiating membrane repair and transfection efficiency in vitro.

A. Effects of Radiation on Tissue

The use of radiation therapy in the treatment of tumors is now a well-established and well-accepted clinical practice. However, it is also well established that serious complications can arise in human patients treated with radiation. Normal tissues within a radiation treatment field can be expected to suffer radiation-induced damage, and the probability of normal tissue injury is dose-related. The deposition of radiant energy is random and discrete, and thus cell killing by radiation approximates an exponential function of dose (5).

There are two common causes of cell death following exposure to ionizing radiation; loss of reproductive capability by virtue of injury to the cell's genetic apparatus, and "interphase death", which is caused by damage to the membranes of cells in the irradiated tissue. With regard to the former, experimental evidence indicates that DNA is the critical target. This injury to DNA is expressed when a cell attempts mitotic division; at some point in its reproductive life the irradiated cell will be incapable of undergoing mitosis, and therefore it is considered to have been sterilized by irradiation (5). Interphase death is manifested by tissue edema and, frequently, by cell necrosis, with resulting local pain, fistulas, ulcers, and in some cases permanent tissue damage. One aspect of the present invention addresses the prevention and/or treatment of interphase death.

Although naturally occurring cell repair has been demonstrated following radiation injury, and despite the fact that the volume of tissue injury can be controlled (to an extent) by variation of the size, number, and quality of radiation treatments, to date a reliable means whereby tissue damage may be prevented or repaired has yet to be developed. Administering unduly conservative radiation treatments can decrease the amount of damage sustained by normal tissue, but will necessarily increase the number of patients experiencing failure of tumor control. On the other hand, use of excessive doses of radiation will increase the number of patients experiencing radiation-induced injuries to normal tissue (5). Therefore, a significant need exists for a prophylactic and/or therapeutic means of reducing and/or treating membrane damage caused by exposure to radiation. In fact, it should be noted that accidental or other non-therapeutic exposures to radiation can also be expected to cause significant tissue injury due to cell membrane permeabilization, and a method for treating such damage should also be considered an important development.

B. Tissue Injury in Freeze-Thaw Injuries (Frostbite)

Cellular damage resulting from freezing results from two primary physical effects. As the temperature is lowered ice crystals form in the cytoplasm. Water in the form of ice is less dense than liquid water, thus the cell expands resulting in membrane disruption. Secondly, solidification of water excludes solutes present in the liquid form. During ice crystal growth, the surrounding liquid water becomes excessively concentrated. High concentrations of salts can denature and damage proteins, including the cell membrane proteins. Thus, damage to the membrane appears to be the most important event in freeze injuries.

It has been shown that antisludging agents, including Pluronic F-68, a copolymer of polyoxyethylene and polyoxypropylene glycol (a poloxamer), and dextran, are capable of diminishing the development of fat embolisms and decreasing platelet adhesiveness, thereby improving blood flow to frostbite affected areas (6). However, there is no method of treatment which combines the membrane protective/restorative properties of surface active copolymers with the energy store recharging capabilities of high energy phosphate compounds. Therefore, a means of repairing cell membrane damage, or minimizing the likelihood of any initial cell membrane damage through prophylactic treatment while re-establishing the cellular energy charge, would be a novel and useful development which should lead to significantly improved recovery of frostbite-injured tissue.

C. Enhanced Cell Survival and Transfection Following Membrane Permeabilization

Several techniques are available whereby foreign macromolecules, such as DNA or antisense molecules for antisense therapy, can be introduced into eukaryotic cells. One of the most common methods for incorporation of exogenous molecules into living cells depends upon the permeabilization of the cell membrane. Cell membrane permeabilization involves the creation of numerous discrete openings in the cell membrane, and can be achieved using detergents, by changing osmotic conditions, or through mechanical or electrical means. However, such permeabilization causes significant cell injury and can lead to cell death, leading to unacceptably low cell survival rates following transfection or antisense therapy.

Although methods have been described which avoid or reduce the deleterious effects of cell membrane permeabilization, each suffers from particular limitations. The addition of serum to cells permeabilized through the use of electrical pulses has been shown to enhance cell survival as well as transfection efficiency (7). Furthermore, when cells are transfected without membrane permeabilization, it has been shown that the use of lipopolyamine-coated plasmid promotes transfection without significant deleterious side effects (8,9). However, not all cell systems are amendable to transfection without permeabilization, and serum may contain factors which could interfere with experimental protocols or which could influence results.

Accordingly, a method whereby the efficiency of permeabilization-mediated transfection could be enhanced and cell survival could be increased using an inert substance to promote transfection and membrane repair would be a useful and unique development in molecular genetics, particularly in cell systems which are resistant to viral and chemical transfection methods.

D. Biological Applications of Surface Active Copolymers

Several biomedical applications of surface active copolymers, and in particular poloxamers, have been described. These include use as an agent in the preparation of stable and concentrated antiserum, as an emulsifying agent, as a wetting agent in an antiseptic skin cleaning formulation, as an enhancer of drug or antibiotic levels in the blood, and as a tool in the study of tumor metastasis (10).

Specifically, poloxamer 188 has been used as an emulsifying agent since the 1950s. Initially it was used as a surfactant to protect red blood cells in the membrane oxygenators of early model cardiopulmonary bypass machines, and was shown to prevent hemolysis and lipid embolism. It has been used as an emulsifying agent in foods, oral drugs and cosmetics and is an FDA-approved food additive. Poloxamer 188 has been shown to block the adhesion of fibrinogen to hydrophobic surfaces and the subsequent adhesion of platelets and red blood cells. It is currently an FDA-approved surfactant in the synthetic blood replacement flusol (11). (See also U.S. Pat. Nos. 4,879,109, 4,897,263, and 4,937,070, incorporated herein by reference).

As noted, a particular need exists for a safe and effective method of prophylaxis and/or treatment of cell membrane damage, and the tissue damage which results therefrom, caused by radiation, freezing, and various subtypes of mechanical injury. Decreases in therapeutic radiation doses and protracted radiation treatment regimens are inadequate because too low a dose may be ineffective to control tumor growth, and extended treatment can result in more severe chronic normal tissue injury (5). Both radiation and frostbite can cause severe necrotizing tissue injury due to cell membrane permeabilization, and no immediately effective method for preventing or treating such injuries currently exists. The present invention relates to such a method.

Furthermore, a significant need exists in the field of molecular genetics for a means of increasing cell survival rates and transfection efficacy. Although it has been suggested that whole, undialyzed serum can perform these functions, at least to an extent (7), whole serum may possess biological activities which could militate against its use in many experimental protocols. The present invention, in a particular embodiment, relates to a method whereby a biologically inert surface active copolymer, in particular a poloxamer, is effective in enhancing cell survival and transfection efficacy.

SUMMARY OF THE INVENTION

The present invention recognizes the critical importance of maintaining cell membrane integrity in order to prevent tissue damage, particularly due to radiation, freezing and thawing, or mechanical disruptions, or to improve cell survival rates following membrane permeabilization in vitro. The method of the invention involves the use of a surface active copolymer, for example a poloxamer, to minimize tissue damage or to potentiate the healing process. In instances where cells are permeabilized in order to transfect the cells with an exogenous macromolecule (e.g., DNA, antisense molecules, proteins) the present invention also embodies the realization that a surface active copolymer can also enhance the efficacy of the transfection. The present invention also recognizes the potential for enhanced recovery of damaged tissue where one desires to re-establish cell membrane integrity as rapidly as possible. Therefore, the invention embodies a collection of methods whereby cell membrane damage can be either minimized or more rapidly repaired through the use of pharmaceutical compositions containing a surface active copolymer.

Depending upon the nature of the injury and the nature of the use of the copolymer (i.e., whether the use is prophylactic or for treatment of an injury), the pharmaceutical composition containing the copolymer can be administered intravenously, intramuscularly, subcutaneously or topically. Furthermore, the present invention embodies a dramatic and unique realization that high energy phosphate compounds can potentiate the benefits which result from membrane repair by restoring cellular metabolic functions.

The present invention is thus directed in general to methods of prophylaxis and treatment of tissue damage resulting, at least in part, from permeabilization of the membranes of the cells which make up the damaged tissue. The use of a pharmaceutical composition of a surface active copolymer, and, in a preferred embodiment, a poloxamer, which may also contain high energy phosphate compounds which can potentiate the healing process by re-establishing cellular energy stores, constitutes such a method.

Accordingly, one aspect of the invention is directed to a method of reducing tissue damage caused by radiation wherein the irradiated tissue is treated either before, during, or after exposure to the radiation source with an effective amount of a composition comprising a surface active copolymer. Animal or human tissue can be treated, and the exposure to the radiation may be through either accidental exposure, experimental exposure, or through therapeutic exposure during radiation therapy. The form of the radiation is either ionizing or non-ionizing, and in accordance with a preferred embodiment, a high energy phosphate compound such as $ATP-MgCl_2$ or phosphocreatine is administered in combination with the surface active copolymer. Administration may be either intravenously, intramuscularly, or topically.

The surface active copolymer, in a preferred embodiment, comprises a poloxamer with a molecular weight of at least 2,000 and not more than 20,000 Daltons. According to a preferred embodiment, the poloxamer's hydrophobic group has a molecular weight of approximately 950–4,000 Daltons, and its hydrophilic groups constitute approximately 45–95% by weight of the poloxamer. According to a further preferred embodiment, the hydrophobic group has a molecular weight of 1,750–3,500 Daltons, and the hydrophilic groups constitute approximately 50–90% by weight of the poloxamer. As will be presented in further detail below, the molecular weight of the poloxamer itself and of the hydrophobic group, and the relative weight of the hydrophilic group are critical in determining the physical properties of the poloxamer, the more important of which include its solubility in water and its characteristics when interacting with hydrophobic groups in the cell membrane.

Another embodiment of the present invention is use of a composition comprising a surface active copolymer in combination with a high energy phosphate compound in treating or preventing frostbite.

A further aspect of the present invention is directed toward a method for enhancement of cell survival following membrane permeabilization, and involves the administration of a composition comprising a surface active copolymer to the incubation medium before, during, or after the permeabilization. Permeabilization may be accomplished through osmotic means, by detergent application, or by mechanical means. In a preferred embodiment of this aspect of the invention, the composition containing the surface active copolymer also contains a high energy phosphate compound such as $ATP-MgCl_2$ or phosphocreatine.

A further aspect of the present invention is more specifically directed toward a method for increasing the efficiency by which exogenous molecules are incorporated into cells. Before, during, or after permeabilization and transfection, the cells are exposed to a composition comprising a surface active copolymer. In a preferred embodiment of the invention, the exogenous molecule being transfected into the cell would be DNA, and according to a further preferred embodiment, the composition containing the surface active copolymer would also contain a high energy phosphate compound such as $ATP-MgCl_2$ or phosphocreatine.

DETAILED DESCRIPTION OF THE INVENTION

In a very simplistic model of membrane repair it could be postulated that upon permeabilization (opening at numerous sites) of the cell membrane, both the hydrophobic region of membrane protein and the hydrophobic tails of the membrane's lipid bilayer are exposed to the more polar, aqueous environments of the extracellular fluid and the cell cytoplasm. Cytoskeletal elements typically located at or near the internal layer of the cell membrane might be expected to react in such a way as to form at least a partial barrier to the escape of intracellular organelles and compartments. However, ions would be expected to both escape from and enter into the cell down their concentration gradients, and other small molecules can probably pass through the patencies. In fact, if the extent of the damage to the cell membrane were severe, it could be envisioned that a significant amount of cytoplasm, including macromolecules and small organelles, might leak out of the cell.

The lipid molecules in the membrane bilayer nearest the openings would be expected to respond to exposure to the polar environment by reorienting themselves such that their hydrophilic head groups would turn toward the polar solution at the point of exposure. This would isolate the hydrophobic tails of the lipid molecules within the membrane from the aqueous intra- and extracellular space. Membrane fusion and repair of the patencies would occur as the newly formed hydrophilic edges of the patencies move into apposition to each other (8). A method whereby such a mechanism could be potentiated, especially if the method provided the means for restoring the permeabilized cells' energy charge, would be a boon to the treatment and prevention of injuries involving, at the cellular level, cell membrane permeabilization. The present invention relates to such a method.

A. Surface Active Copolymers

Surface active copolymers, or block polymer nonionic surfactants, are surface active agents prepared by the sequential addition of two or more alkylene oxides to a low molecular weight water soluble organic compound containing one or more active hydrogen atoms. There are four groups of surface active copolymers of particular importance with regard to the present invention: the poloxamers, the meroxapols, the poloxamines and the PLURADOT® polyols. There is a good deal of intergroup variation with respect to the polymers' synthesis, although in all syntheses the oxyalkylation steps are carried out in the presence of an alkaline catalyst, generally sodium or potassium hydroxide. The alkaline catalyst is then neutralized and typically removed from the final product.

The poloxamers are synthesized by the sequential addition of propylene oxide, followed by ethylene oxide, to propylene glycol, which in the case of the poloxamers constitutes the water-soluble organic component of the polymer. The inner polyoxy-propylene glycol is the hydrophobic portion of the poloxamer. This is due to the fact that this group changes from a water-soluble to a water-insoluble polymer as the molecular weight goes above 750 Daltons. Adding ethylene oxide in the final step makes the molecule water-soluble.

As noted earlier, in a preferred embodiment of the invention the use of a poloxamer with a molecular weight of at least 2,000 and not more than 20,000 Daltons is envisioned. This molecular weight range is important in maintaining the appropriate solubility of the poloxamer in water while minimizing or eliminating any potential toxicity. Furthermore, the poloxamer's hydrophobic group should have a molecular weight of approximately 950–4,000 Daltons, and its hydrophilic groups should constitute approximately 45–95% by weight of the poloxamer. More preferably, the hydrophobic group should have a molecular weight of 1,750–3,500 Daltons, and the hydrophilic groups should constitute 50–90% by weight of the molecule. Again, as will be discussed in greater detail below, the relative amounts of hydrophile and the molecular weight of the hydrophobe are critical to several of the poloxamer's properties, including its solubility in water and its interactions with hydrophobic groups, and the ranges taught in the present invention provide the maximum effectiveness currently known while minimizing or eliminating toxicity.

When the order of addition of the alkylene oxides is reversed, the meroxapol series is produced. In this series, ethylene glycol is the initiator, and as opposed to the poloxamers, which are terminated by two primary hydroxyl groups, the meroxapols have secondary hydroxyl groups at the ends and the hydrophobe is split in two, each half on the outside of the surfactant.

The poloxamines are prepared from an ethylene diamine initiator. They are synthesized using the same sequential order of addition of alkylene oxides as used to synthesize the poloxamers. Structurally, the poloxamines differ from the other polymers in that they have four alkylene oxide chains, rather than two, since four active hydrogens are present in the initiator. They also differ from the other surfactants in that they contain two tertiary nitrogen atoms, at least one of which is capable of forming a quaternary salt. The poloxamines are also terminated by primary hydroxyl groups.

The PLURADOT® polyols (a quad-block surfactant composed of a block co-polymer of trimethylolpropane attached to three blocks of polyoxyethylene can be prepared from a low molecular weight trifunctional alcohol, such as glycerine or trimethylpropane, which is oxyalkylated initially with a blend of propylene and ethylene oxides, but primarily with propylene oxide, to form the hydrophobe. This is followed by oxyalkylating with a blend of ethylene and propylene oxiles, but primarily ethylene oxide, to form the hydrophile. This group of surfactants has three chains, one more than the poloxamer and meroxapol series, but one less than the poloxamine polymers.

The hydrophilic and hydrophobic chains of the surface active copolymers each have unique properties which contribute to the substances' biological activities. With regard to poloxamers in particular, the longer the hydrophilic polyoxyethylene chains are, the more water the molecule can bind. As these flexible chains become strongly hydrated they become relatively incompressible and form a barrier to hydrophobic surfaces approaching one another. The hydrophobic component of the poloxamers is typically large, weak and flexible.

In any of the surface active copolymer series, as the percent of ethylene oxide increases, or the molecular weight of the hydrophobe decreases, the solubility of the molecule in water increases. Of the four groups of copolymers only the meroxapol polymers exhibit any solubility in mineral oil. The higher the hydrophobic molecular weights, the less soluble the copolymer will be in an organic solvent, and the same is true for those polymers with higher ethylene oxide or propylene oxide concentration. The molecular weight of the hydrophobe will also affect the wetting time of any one species, and the ethylene oxide/propylene oxide ratio of the molecule will influence the foaming properties of that copolymer. A copolymer's emulsification properties may correlate with hydrophobe molecular weights, and toxicity decreases as the ethylene oxide/propylene oxide ratio increases and as the molecular weight of the hydrophobe increases.

All four nonionic series are alike in that they derive their solubility in water from hydrogen bond formation between the many oxygen atoms on the copolymer and protons in the water. As the temperature of a solution containing a nonionic surfactant is raised, the hydrogen bonds are broken and the copolymer clouds out of solution. For example, for poloxamers the 1% cloud point ranges from a low of 14° C. to a high of 100° C., the latter figure being the cloud point for the most hydrophilic polymers. The poloxamines are similar structurally to the poloxamers, and their cloud point range is similarly wide. On the other hand, the meroxapols have a much narrower cloud point range, and the PLURADOT® polymers have the lowest maximum cloud point, primarily due to their lower ethylene oxide content.

Although others have postulated that the ability of the modified poloxamer 188 to form single molecule micelles may play a role in reducing the adhesive properties of damaged cell membranes, the current invention is the first to recognize that surface active copolymers are capable of preventing or minimizing cell membrane permeabilization and repairing permeabilized membranes. It has been suggested that the hydrophobic central domain of the polymer may bind to the hydrophobic portion of the lipid bilayer when these groups are exposed following removal of the external layer of the membrane. The manner in which the poloxamer is folded when this binding occurs has been postulated to assist in the restoration of a non-adhesive cell surface. However, the present invention recognizes that poloxamers are surprisingly capable not merely of restoring a non-adhesive surface, but actually of repairing or potentiating the repair of complete permeations of the entire membrane bilayer.

B. Treatment of Radiation Injuries

In accordance with one aspect of the invention, a pharmaceutical composition of a surface active copolymer is administered either before, during or after exposure to radiation. Exposure to radiation sources is known to cause cell membrane damage. Such damage typically manifests itself by causing tissue edema and, frequently, cell necrosis, with resulting permanent tissue damage. In particular, ionizing radiation, which is the most commonly used type of radiation in cancer therapy, is a form of radiation consisting of subatomic particles (protons, neutrons, or electrons, for example) or electromagnetic waves which is capable of producing ionization (the loss or gain of electrons) directly or indirectly, in its passage through matter (for example, human tissue). The source of the radiation exposure could be something other than a therapeutic source; it could be accidental exposure in the workplace or from a nuclear power plant. However, a preferred embodiment of the invention relates to prophylactic treatment of cancer patients with the surface active copolymer prior to therapeutic exposure to an ionizing radiation source.

Injection of a pharmaceutical composition comprising a sterile filtered poloxamer in a suitable pharmacological carrier at a dose of between 1 mg per ml of blood volume to 5 mg per ml of blood volume is expected to result in minimization of damage due to exposure to radiation if the injection occurs prior to exposure, or to result in rapid reversal of cell membrane permeabilization if injection occurs during or as soon as possible after exposure to the radiation source. Preferably, the poloxamer has a molecular weight of at least 2,000 but not more than 20,000 Daltons and the total molecular weight of the hydrophobe is approximately 950–4,000 Daltons. The hydrophilic groups constitute approximately 45–95% by weight of the poloxamer. More preferably, the hydrophobe has a molecular weight of approximately 1,750–3,500 Daltons and the hydrophilic groups constitute approximately 50–90% by weight of the poloxamer. In a further preferred embodiment, 1% w/v ATP and 1% w/v $MgCl_2$ are co-administered with the poloxamer. In an alternative preferred embodiment, approximately 10% w/v phosphocreatine, a phosphoric acid derivative of creatine which contains an energy-rich phosphate bond, is used in place of ATP-$MgCl_2$ as the high energy phosphate compound. Intramuscular injection is also appropriate, with a poloxamer concentration of 1–10% w/v, and, in a preferred embodiment, ATP at a concentration of 1% w/v and $MgCl_2$ at a concentration of 1% w/v, or phosphocreatine at a concentration of approximately 10% w/v.

For topical administration, the poloxamer is presented in a pharmacologically appropriate substrate at a concentration of 1–10% w/v, and in a preferred embodiment, ATP and $MgCl_2$ are present along with the poloxamer at an appropriate concentration of 1% w/v and 1% w/v respectively. Phosphocreatine at a concentration of approximately 10% w/v could be used as an alternative to ATP and $MgCl_2$. The sterile substrate containing the poloxamer and high energy phosphate compound is applied to the damaged area, wrapped as appropriate with sterile dressings, and is reapplied as necessary. Either topical administration or intravenous administration could be supplemented as necessary with the other form of administration in cases where dual administration is required.

C. Treatment of Tissue Damage Caused by Frostbite

Another embodiment of the invention involves a method for the prevention or treatment of frostbite. Frostbite begins with stinging or aching and progresses to numbness, typically in the extremities. Involved areas appear white and waxy, and during rewarming the skin becomes hyperemic and is very painful. Tissue necrosis may result and may be severe enough to require debridement or amputation. Intravenous administration of a pharmaceutical composition of a poloxamer in combination with a high energy phosphate compound in a suitable pharmacological carrier is performed either before, during or after exposure to temperatures and/or conditions sufficient to cause frostbite.

In a preferred embodiment, an amount of poloxamer constituting 1–5 mg/ml blood volume is administered intravenously as early as possible following diagnosis of frostbite. The poloxamer is co-administered with a high energy phosphate compound, for example, ATP-$MgCl_2$ at a concentration of 1% w/v and 1% w/v, respectively, or phosphocreatine at a concentration of approximately 10% w/v. This allows for concomitant re-establishment of the cellular energy charge along with repair of the cell membrane, enhancing cell survival following the frostbite injury. In a preferred embodiment of the invention, the poloxamer constitutes an ethylene oxide-propylene oxide condensation product wherein the hydrophobic groups have a molecular weight of approximately 950–4,000 Daltons and the hydrophilic portions constitute approximately 45–95% by weight of the poloxamer. In a further preferred embodiment, the hydrophilic group has a molecular weight of approximately 1,750–3,500 Daltons and the hydrophilic portion constitutes approximately 50–90% by weight of the compound. An alternative useful practice of the present invention is the application of the poloxamer topically in a sterile substrate which also contains a high energy phosphate compound such as ATP-$MgCl_2$ or phosphocreatine, the respective concentrations of such phosphate compounds being 1% w/v ATP and 1% w/v $MgCl_2$, and approximately 10% w/v phosphocreatine, in the topically applied compound. The concentration of poloxamer in the topically applied compound is in a range from between 1% and 10% w/v.

D. Enhancement of Permeabilized Cell Survival and Transfection Efficacy

A further embodiment of the invention is directed to a method for enhancing cell survival following cell membrane permeabilization in vitro. Cells in culture may be permeabilized by osmotic disruption, through the use of detergents, or by mechanical disruption. Such permeabilization may be performed for fusion of cells to prepare heterokarya, hybridomas, or hybrid embryos; to insert proteins or other macromolecules into cell membranes; to improve drug delivery; or to introduce plasmids or foreign DNA into living cells for gene transfection. Addition of 0.1–1.0 mg per ml of poloxamer before, during, or after permeabilization is expected to increase cell survival rates. Furthermore, the addition of 1% w/v ATP and 1% w/v $MgCl_2$, or approximately 10% w/v phosphocreatine is expected to have a significant restorative effect on the intracellular energy charge thus further enhancing cell survival following membrane permeabilization. The ethylene oxide-propylene oxide condensation product (the poloxamer) is preferably one with the hydrophobic group having a molecular weight of approximately 950–4,000 Daltons and a hydrophilic portion constituting approximately 45–95% by weight of the compound. In a further preferred embodiment, the hydrophobic group has a molecular weight of approximately 1,750–3,500 Daltons and the hydrophilic portion constitutes approximately 50–90% by weight of the compound.

The present invention is also directed to a method for increasing the efficiency by which exogenous molecules may be incorporated into cells in vitro. In a preferred embodiment cells would undergo membrane permeabilization and transfection with DNA. A medium containing 0.1 mg/ml Pluronic F-68 or poloxamer 1107 is sufficient to enhance the efficacy of the transfection as well as increase the rate of cell survival. As is the case with cell survival, transfection efficacy is further enhanced when the medium contains, in addition to the Pluronic F-68 or poloxamer 1107, a high energy phosphate compound capable of restoring the cells' energy charge, for example 1% w/v of ATP and 1% $MgCl_2$, or 10% w/v phosphocreatine.

The following examples are presented to describe preferred embodiments and utilities of the present invention and are not meant to limit the present invention unless otherwise stated in the claims appended hereto.

EXAMPLE 1

The present example discloses a proposed method of preventing or minimizing cell membrane permeabilization and resulting tissue injury in a patient receiving ionizing radiation treatments for cancer. For purposes of this example, the patient presents following surgical removal of a neck tumor with positive nodes in the middle and lower cervical regions, an indication that the disease has broken through the capsule of nodes.

The patient is prepared in the usual manner for treatment. For purposes of this example, it is assumed that the patient is receiving at least a 200 rad dose fraction five times a week for eight weeks. It is proposed that 1–5 mg/ml blood volume of sterile, Millipore filtered poloxamer 188 or 1107 (available from BASF Co., Parsippany, N.J.) or RheothRX™ (a formulation of poloxamer 188 available from CytRx® Corp., Atlanta, Ga.) in a pharmaceutically appropriate carrier (e.g., sterile water or buffered saline) would be injected into a suitable vein immediately preceding the administration of the radiation dose.

Alternatively, the pharmaceutical composition of poloxamer 188 or 1107 would be injected intramuscularly, again immediately prior to administration of the radiation dose. In the case of either intravenous or intramuscular injection, the pharmaceutical composition of the poloxamer may contain, in addition, 1% w/v ATP and 1% w/v $MgCl_2$, or 10% w/v phosphocreatine so that the healing of any membrane damage which might have occurred can be potentiated through the recharging of cellular energy stores.

Depending upon the treatment history of any one patient, normal tissue damaged during radiation therapy can also be treated using an appropriate pharmaceutical composition containing a poloxamer. A patient presenting with soft tissue necrosis with local pain, fistulas or ulcers is to be treated by intravenous injection of 1 to 5 mg/ml blood volume of sterile, Millipore filtered poloxamer 188 or 1107 in a pharmaceutically acceptable carrier. Injection may be repeated daily as appropriate depending upon the severity of the necrosis, the amount and intensity of radiation therapy still to be performed, and the response of the individual to the poloxamer treatments. The pharmaceutical composition of poloxamer may also contain 1% w/v ATP and 1% w/v $MgCl_2$, or 10% w/v phosphocreatine to potentiate cell membrane repair through the reestablishment and maintenance of the cells' energy charge.

Alternatively, 1 to 10% w/v poloxamer 188 or 1107 is suspended in a pharmaceutically appropriate sterile ointment (e.g., an oil-in-water type emulsion base) or in sterile water in an aerosol container for direct topical application to the injured tissue. The site of injury would then be bandaged with appropriate dressings, and the poloxamer suspension reapplied as necessary. In addition, the poloxamer suspension for topical application could also contain a high energy phosphate compound for recharging of cellular energy stores and further potentiation of cell repair. Phosphocreatine (10% w/v) or ATP (1% w/v) and $MgCl_2$ (1% w/v) are examples of preferred high energy phosphate compounds. Depending upon the severity and depth of the tissue injury, the poloxamer and high energy phosphate compounds could be coadministered to the same patient both parenterally and topically. In this way, deep tissue injuries can be treated through parenteral administration, and surface lesions treated directly by topical application. Dose and application regimen need not be varied in cases where oral application is indicated.

EXAMPLE 2

The present example discloses a method of treatment of tissue damage caused by frostbite. For purposes of this example the patient presents with frostbite-related tissue necrosis. Sterile, millipor filtered poloxamer 188 or 1107 in a pharmaceutically appropriate carrier at a final concentration of 2–8 mg/ml blood volume is injected intravenously or subcutaneously or intramuscularly near the affected area. In addition, the pharmaceutical composition containing the poloxamer would also contain a high energy phosphate compound for the restoration of cellular energy stores in the injured tissue. Phosphocreatine at a concentration of 10% w/v, or ATP (1% w/v) and $MgCl_2$ (1% w/v) are suitable high energy compounds. Depending upon the severity of the injury and the initial response to treatment, the administration may be repeated on a daily basis.

Alternatively, a pharmaceutical suspension of poloxamer 188 or 1107 in an appropriate sterile ointment, or in sterile water in an aerosol container, with a final poloxamer concentration of 1–10% w/v in either case, could be applied topically to the injured tissue. The damaged area is then bandaged, and the poloxamer suspension is reapplied as necessary based on the response to treatment and the severity of the injury up to 6 times per day every 4 hours. Additionally, the topically applied poloxamer suspension would also contain a high energy phosphate compound for recharging cellular energy stores and accelerating the healing process. The suspension would also contain 1% w/v ATP and 1% w/v $MgCl_2$, or 1% w/v phosphocreatine. The invention also proposes the combined use of parenterally and topically administered poloxamer 188 or 1107, with or without a high energy compound, depending upon the extent and severity of the frostbite damage. For combined use the dosages and administration regimens presented above need not be adjusted.

EXAMPLE 3

The present example discloses a method for increasing cell survival rates following in vitro permeabilization of cell membranes. The permeabilization may be performed either to introduce exogenous macromolecules into the permeabilized cells, such as in the introduction of antisense molecules in antisense therapy, or to transfect the cells with exogenous DNA.

For purposes of this example, cells of a murine myelomonocytic leukemia line are grown in a Modified McCoys 5A medium with 10% fetal bovine serum (HyClone) at 37° C. in 5% $CO_2$ in air. Cells are resuspended in HeBS buffer consisting of 20 mM Hepes pH 7.05, 137 mM NaCl, 5 mM KCL, 0.7 mM $Na_2HPO_4$, and 6 mM dextrose. Cell density for permeabilization is approximately $3 \times 10^6$ cells/ml, and plasmid DNA in supercoiled form is added to a final concentration of 50 µg/ml. Permeabilization can be performed mechanically (e.g., by sonication), using a detergent, (e.g., SDS or Triton X-100), or by changing the osmotic conditions of the medium.

After permeabilization and transfection have proceeded for approximately 5–10 minutes, 0.1–1.0 mg/ml poloxamer 188 or 1107 is added to the medium in order to potentiate both membrane repair, and thus cell survival, and efficiency of transfection. In addition, a high energy phosphate compound is added to the medium with the poloxamer so that the permeabilized cells' energy stores are recharged. This will further potentiate repair and survival. Phosphocreatine at a concentration of 10% w/v, or 1% w/v ATP and 1% w/v $MgCl_2$ may be added for this purpose.

REFERENCES

1. Chaudry, et al. "Effect of Adenosine TriphosphateMagnesium Chloride Administration in Shock," *Surgery* 75:220–227 (1974).
2. Aldwinckle, et al., "Effects of Poly(ethylene glycol) in Liposomes and Erythrocytes Permeability Changes and Membrane Fusion," *Biochem. Biophys. Alta* 689:548–560 (1982).
3. Papahadiopoulos, et al., "Molecular Mechanisms of Calcium-Induced Membrane Fusion," *J. Bioenergetics Biomembranes* 22:157–179 (1990).
4. McNeil, "Cell Wounding and Healing," *Am. Scientist*, 79:222–235 (1991).
5. Peters, "Biology of Radiation Therapy," in *Comprehensive Management of Head and Neck Tumors*, Thawley and Panje, eds., W. B. Saunders Co., 1987, pp. 132–152.
6. Kinze, et al., "Use of Antisludging Agents in Experimental Cold Injuries," *Surg. Gyn. & Obst.* 129:1019–1026 (1969).
7. Bahnson and Boggs, "Addition of Serum to Electroporated Cells Enhances Survival and Transfection Efficiency," *Biochem. Biophys. Res. Comm.* 171:752–757 (1990).
8. Behr, et al., "Efficient Gene Transfer into Mammalian Primary Endocrine Cells with Lipopolyamine-coated DNA," *Proc. Nat'l. Acad. Sci.* 86:6982–6986 (1989).
9. Loeffler, et al., "Lipopolyamine-Mediated Transfection Allows Gene Expression Studies in Primary Neuronal Cells," *J. Neurochem.* 54:1812–1815 (1990).
10. Schmolka, "A Review of Block Polymer Surfactants," *J. Am. Oil Chemists' Soc.* 54:110–116 (1977).
11. Check and Hunter, "The Scientific Basis for the Biologic Activities of RheothRx™ Copolymer: A Rheologic, Antithrombotic and Cytoprotective Preparation," CytRx Corp., 1988.

What is claimed is.

1. A method of reducing animal tissue damage due to radiation comprising treating tissue with a composition consisting essentially of an amount of a surface active copolymer, selected from the group consisting of poloxamer, meroxapol, poloxamine and a polyol of trimethylolpropane and polyoxyethylene, that is effective to reduce radiation damage to said tissue by stabilizing cellular membranes or reducing membrane permeability, the surface active copolymer having a molecular weight of between about 2,000 and about 20,000 Daltons and from about 45% to 95% hydrophobic groups by weight of the copolymer; a high energy phosphate compound; and a pharmaceutically acceptable carrier, wherein said composition is administered either before, during or after the tissue's exposure to a radiation source.

2. The method of claim 1 wherein said radiation is ionizing radiation.
3. The method of claim 1 wherein said radiation is nonionizing radiation.
4. The method of claim 1 wherein the method is practiced on a human subject.
5. The method of claim 4 further defined as a method for reducing the tissue damage in a human subject undergoing radiation therapy, the method comprising the steps of:
   (a) identifying a patient who is about to undergo radiation therapy; and
   (b) administering to said patient an effective amount of the surface active copolymer before, during or after the therapy.
6. The method of claim 4 further defined as a method for reducing the tissue damage in a human subject undergoing radiation therapy, the method comprising the steps of:
   (a) identifying a patient who has undergone radiation therapy and has suffered damage to nondiseased tissues as a consequence thereof; and
   (b) administering to said patient an effective amount of the surface active copolymer in order to treat said damaged nondiseased tissue and to prevent or minimize further damage to said nondiseased tissue.
7. The method of claim 1 wherein the high energy phosphate compound comprises $ATP-MgCl_2$.
8. The method of claim 1 wherein the high energy phosphate compound comprises phosphocreatine.
9. The method of claim 1 wherein the composition is administered to a subject intravenously, intramuscularly or topically in order to treat the affected tissue.
10. The method of claim 1 wherein the poloxamer has the following general formula:

wherein a is an integer such that the hydrophobe represented by $(C_3H_6O)_a$ has a molecular weight of approximately 950 to 4,000, and b is an integer such that the hydrophile represented by $(C_2H_4O)_b$ constitutes approximately 45% to 95% by weight of the poloxamer.

11. The method of claim 1 wherein the poloxamer has the following general formula:

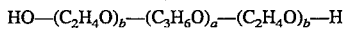

wherein a is an integer such that the hydrophobe represented by $(C_3H_6O)$ has a molecular weight of approximately 1,750 to 3,500, and b is an integer such that the hydrophile represented by $(C_2H_4O)_b$ constitutes approximately 50% to 90% by weight of the poloxamer.

12. A method for repair of permeability damage to cells following membrane permeabilization comprising administering to permeabilized cells, in a dosage form other than topical, a composition comprising an amount of a surface active copolymer, selected from the group consisting of poloxamer, meroxapol, poloxamine and a polyol of trimethylolpropane and polyoxethylene, that is effective to stabilize the membranes of said cells or reduce their permeability, the surface active copolymer having a molecular weight of between about 2,000 and about 20,000 Daltons and from about 45% to 95% hydrophobic groups by weight of the copolymer, the copolymer being administered before, during or after membrane permeabilization.

13. The method of claim 12 wherein membranes of said cells are permeabilized by irradiation, by osmotic means, by use of a detergent, or by mechanical means.

14. The method of claim 12 wherein said composition further comprises a high-energy phosphate compound.

15. The method of claim 14 wherein the high-energy phosphate compound comprises $ATP-MgCl_2$.

16. The method of claim 14 wherein the high-energy phosphate compound comprises phosphocreatine.

17. The method of claim 12 further comprising incorporating exogenous macromolecules into the permeabilized cells.

18. The method of claim 17 wherein said exogenous molecules are DNA molecules, and wherein the DNA molecules are incorporated into the cell by transfection.

19. The method of claim 17 wherein the exogenous macromolecules comprise DNA antisense molecules.

20. A method for increasing the efficiency by which exogenous macromolecules are incorporated into living cells comprising the following steps:

(a) permeabilizing the membranes of the cells;

(b) exposing the cells to the exogenous macromolecules; and (c) either before, during or after the performance of steps (a) and (b), administering to the living cells, in a dosage form other than topical, a composition comprising an amount of a surface active copolymer, selected or from the group consisting of poloxamer, meroxapol, poloxamine and a polyol of trimethylolpropane and polyoxyethylene, that is effective to stabilize the membranes of said cells or reduce their permeabilization, the surface active copolymer having a molecular weight of between about 2,000 and about 20,000 Daltons and from about 45% to 95% hydrophobic groups by weight of the copolymer.

21. The method of claim 20 wherein said exogenous macromolecules comprise DNA molecules, and wherein the DNA molecules are incorporated into the cells by transfection.

22. The method of claim 20 wherein said exogenous macromolecules comprise DNA antisense molecules, and wherein said DNA antisense molecules are incorporated into the living cells by transfection.

23. The method of claim 1, wherein the selected surface active copolymer is a poloxamer.

24. The method of claim 23, wherein the poloxamer is poloxamer 188.

25. The method of claim 23, wherein the poloxamer is poloxamer 1107.

26. The method of claim 1, wherein the selected surface active copolymer is a meroxapol.

27. The method of claim 1, wherein the selected surface active copolymer is a poloxamine.

28. The method of claim 1, wherein the selected surface active copolymer is a polyol of trimethylolpropane and polyoxyethylene.

29. The method of claim 12, wherein the selected surface active copolymer is a poloxamer.

30. The method of claim 29, wherein the poloxamer is poloxamer 188.

31. The method of claim 29, wherein the poloxamer is poloxamer 1107.

32. The method of claim 12, wherein the selected surface active copolymer is a meroxapol.

33. The method of claim 12, wherein the selected surface active copolymer is a poloxamine.

34. The method of claim 12, wherein the selected surface active copolymer is a polyol of trimethylolpropane and polyoxyethylene.

35. The method of claim 20, wherein the selected surface active copolymer is a poloxamer.

36. The method of claim 35, wherein the poloxamer is poloxamer 188.

37. The method of claim 35, wherein the poloxamer is poloxamer 1107.

38. The method of claim 20, wherein the selected surface active copolymer is a meroxapol.

39. The method of claim 20, wherein the selected surface active copolymer is a poloxamine.

40. The method of claim 20, wherein the selected surface active copolymer is a polyol of trimethylolpropane and polyoxyethylene.

* * * * *

UNITED STATES PATENT AND TRADEMARK OFFICE
CERTIFICATE OF CORRECTION

PATENT NO.  : 5,470,568
DATED       : November 28, 1995
INVENTOR(S) : Raphael C. Lee It is certified that error appears in the above-indentified patent and that said Letters Patent is hereby corrected as shown below:

In claim 11, column 14, line 5, delete "$(C_3H_6O)$" and insert -- $(C_3H_6O)_a$ -- therefor.

Signed and Sealed this

Twenty-sixth Day of March, 1996

Attest:

BRUCE LEHMAN

*Attesting Officer*    *Commissioner of Patents and Trademarks*